United States Patent
Levy

(10) Patent No.: US 12,329,410 B2
(45) Date of Patent: Jun. 17, 2025

(54) CANNULATION DEVICES, SYSTEMS, AND METHODS

(71) Applicant: Mazor Robotics Ltd., Caesarea (IL)

(72) Inventor: Arik Levy, Herzliya (IL)

(73) Assignee: Mazor Robotics Ltd., Caesarea (IL)

( * ) Notice: Subject to any disclaimer, the term of this patent is extended or adjusted under 35 U.S.C. 154(b) by 1036 days.

(21) Appl. No.: 17/350,893

(22) Filed: Jun. 17, 2021

(65) Prior Publication Data
US 2022/0047297 A1 Feb. 17, 2022

Related U.S. Application Data

(60) Provisional application No. 63/064,530, filed on Aug. 12, 2020.

(51) Int. Cl.
*A61B 17/34* (2006.01)
*A61B 17/00* (2006.01)

(52) U.S. Cl.
CPC ...... *A61B 17/3423* (2013.01); *A61B 2017/00017* (2013.01); *A61B 2017/00367* (2013.01); *A61B 2017/00398* (2013.01); *A61B 2017/00991* (2013.01); *A61B 2017/3443* (2013.01)

(58) Field of Classification Search
CPC ............ A61B 17/3417; A61B 17/3421; A61B 2017/00991; A61B 2017/3433; A61B 2034/301
See application file for complete search history.

(56) References Cited

U.S. PATENT DOCUMENTS

| | | | |
|---|---|---|---|
| 5,146,921 | A | 9/1992 | Terwilliger et al. |
| 6,086,544 | A | 7/2000 | Hibner et al. |
| 6,342,061 | B1 | 1/2002 | Kauker et al. |
| 7,497,868 | B2 | 3/2009 | Steinberg |
| 7,632,079 | B2 | 12/2009 | Hershberger et al. |
| 8,435,174 | B2 | 5/2013 | Cropper et al. |
| 8,475,432 | B2 | 7/2013 | Moberg et al. |
| 8,852,253 | B2 | 10/2014 | Mafi |

(Continued)

FOREIGN PATENT DOCUMENTS

| | | |
|---|---|---|
| CN | 108144178 | 6/2018 |
| JP | 5164571 | 3/2013 |

OTHER PUBLICATIONS

International Search Report and Written Opinion for International (PCT) Patent Application No. PCT/IL2021/050967, dated Nov. 10, 2021, 15 pages.

*Primary Examiner* — Katherine M Shi
*Assistant Examiner* — Lindsey Bachman
(74) *Attorney, Agent, or Firm* — Sheridan Ross P.C.

(57) ABSTRACT

A cannulation tool, systems, and methods for placing a cannula is provided. The tool includes a body and a plurality of tubes removably secured to the body. Each tube is moveable from a retracted position to an extended position. The plurality of tubes may include an inner tube, an outer tube, and a set of tubes positioned between the inner tube and the outer tube. Each tube of the set of tubes is nested in an adjacent tube, the outer tube is positioned external to the set of tubes, and the inner tube is positioned internal to the set of tubes. The tool also includes a gripper rod having a gripper disposed on an end thereof for forcibly moving each tube of the set of tubes, in sequence, from the retracted position to the extended position.

19 Claims, 7 Drawing Sheets

(56) References Cited

U.S. PATENT DOCUMENTS

| | | |
|---|---|---|
| 9,192,410 B2 | 11/2015 | Whitman et al. |
| 9,883,882 B2 | 2/2018 | Haufe et al. |
| 9,901,370 B2 | 2/2018 | Kim et al. |
| 10,172,642 B2 | 1/2019 | Zook et al. |
| 10,245,070 B2 | 4/2019 | Flom et al. |
| 10,456,208 B2 | 10/2019 | Thompson et al. |
| 10,542,922 B2 | 1/2020 | Sia et al. |
| 10,632,241 B2 | 4/2020 | Schenck et al. |
| 10,646,245 B2 | 5/2020 | Slupchynskyj |
| 2004/0230160 A1* | 11/2004 | Blanco ............... A61B 17/3498 604/167.06 |
| 2005/0124914 A1* | 6/2005 | Dicarlo ............. A61B 10/0275 606/167 |
| 2007/0255305 A1 | 11/2007 | McMichael et al. |
| 2009/0171271 A1* | 7/2009 | Webster ............. A61B 17/3421 604/95.01 |
| 2011/0201887 A1 | 8/2011 | Greenblatt et al. |
| 2014/0066964 A1 | 3/2014 | Mirza et al. |
| 2014/0371532 A1 | 12/2014 | Trovato |
| 2015/0351798 A1 | 12/2015 | Bourland et al. |
| 2016/0206347 A1* | 7/2016 | Bar ....................... A61M 29/00 |
| 2016/0242849 A9 | 8/2016 | Crawford et al. |
| 2016/0346519 A1* | 12/2016 | Bagwell ............. A61B 17/3401 |
| 2017/0095617 A1 | 4/2017 | Koehler et al. |
| 2019/0133676 A1 | 5/2019 | Hsu et al. |
| 2019/0269469 A1* | 9/2019 | Bush, Jr. ................ A61B 34/76 |

* cited by examiner

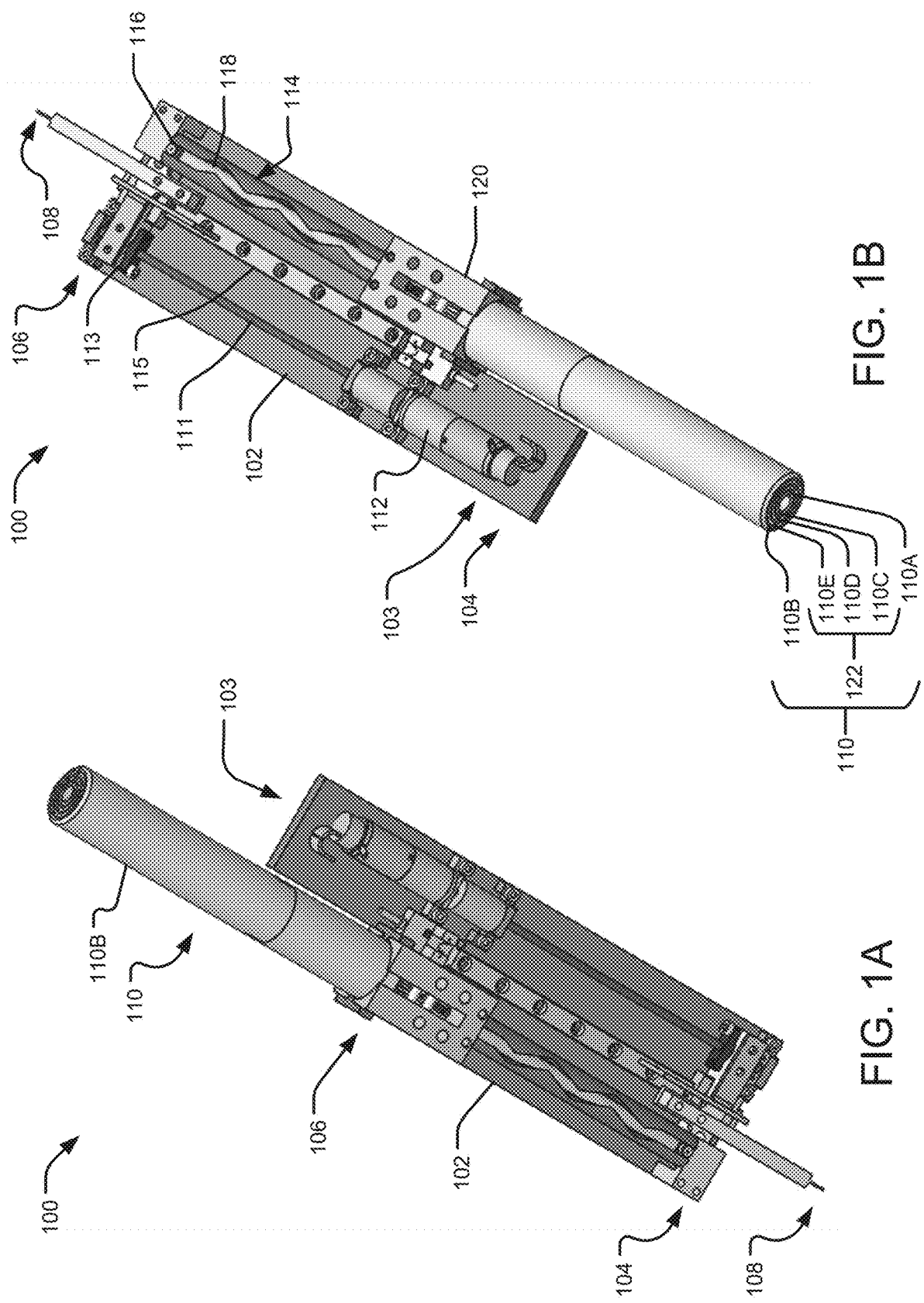

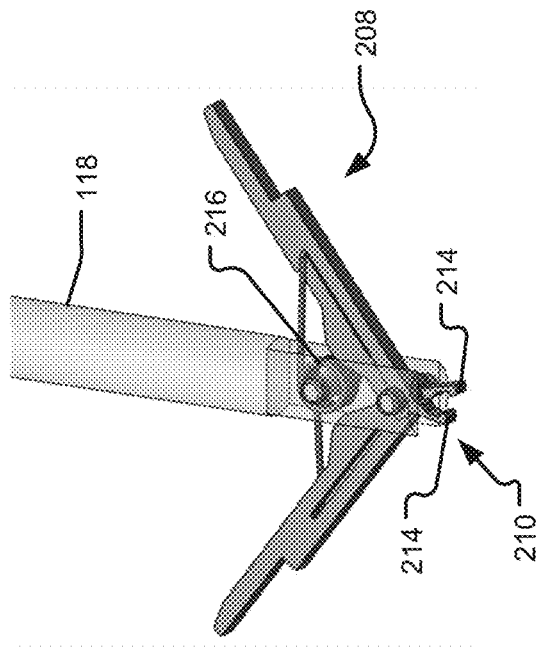
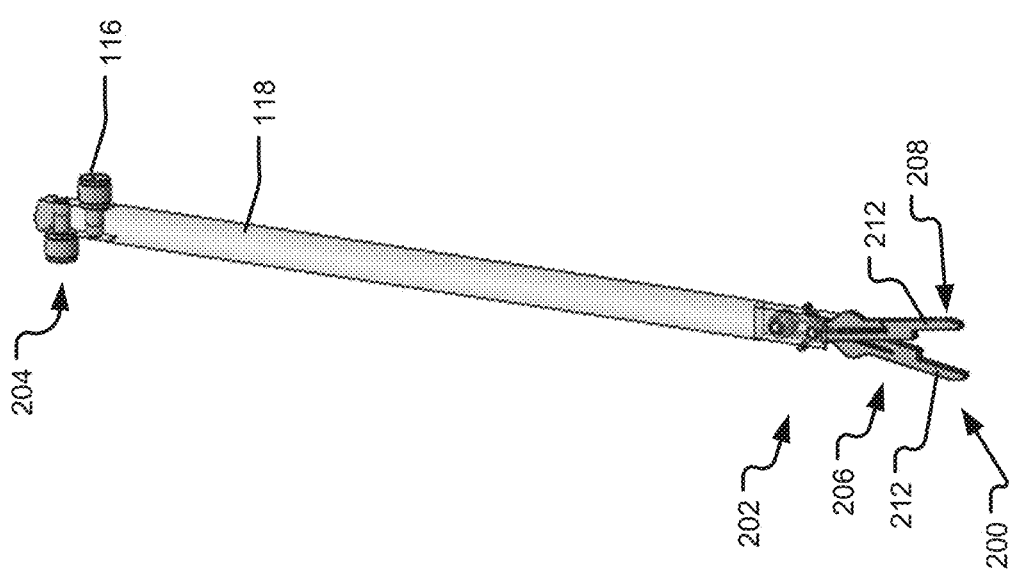

CANNULATION DEVICES, SYSTEMS, AND METHODS

CROSS REFERENCE TO RELATED APPLICATIONS

This application claims the benefit of U.S. Provisional Application No. 63/064,530, filed on Aug. 12, 2020, and entitled "Cannulation Devices, Systems, and Methods", which application is incorporated herein by reference in its entirety.

FIELD

The present technology is related generally to cannulation tubes and the use thereof, and more particularly, to inserting a plurality of cannulation tubes in an opening.

BACKGROUND

Cannulation tubes are used to form and create an open tube access in a patient for the removal or insertion of fluids, samples, or tools. Placing a cannula may be done manually by cutting the skin and inserting increasing dilators and a location of the cannula is based on the type of procedure performed. A cannula may be positioned and left in place for short or long-term duration.

SUMMARY

Example aspects of the present disclosure include:

A cannulation tool according to at least one embodiment of the present disclosure comprises: a body; a plurality of tubes removably secured to the body, each tube moveable from a retracted position to an extended position, the plurality of tubes including an inner tube, an outer tube, and a set of tubes positioned between the inner tube and the outer tube, each tube of the set of tubes nested in an adjacent tube, the outer tube positioned external to the set of tubes, and the inner tube positioned internal to the set of tubes; and a gripper rod having a gripper disposed on an end thereof for forcibly moving each tube of the set of tubes, in sequence, from the retracted position to the extended position.

Any of the aspects herein, wherein the inner tube and each tube of the set of tubes comprises a protrusion on an outer surface thereof, each protrusion configured to engage a groove on an inner circumference of an adjacent tube.

Any of the aspects herein, further comprising a motor configured to cause the gripper rod to selectively extend and retract.

Any of the aspects herein, further comprising an oscillation rail mounted to the body that causes the gripper rod to oscillate during an extension or retraction movement.

Any of the aspects herein, wherein the gripper moves the outer tube from the retracted position to the extended position.

Any of the aspects herein, wherein the gripper moves the inner tube from the retracted position to the extended position.

Any of the aspects herein, wherein the gripper is reconfigurable from a first configuration to a second configuration, the gripper operable to retract both the set of tubes and the inner tube when the gripper is in the second configuration.

Any of the aspects herein, wherein the gripper is biased towards the second configuration.

Any of the aspects herein, wherein the inner tube includes a pin on an inner surface thereof, and further wherein the gripper is configured to grip the pin when the gripper is in the second configuration to retract the plurality of tubes Any of the aspects herein, wherein the outer tube is configured to remain in the extended position when both the set of tubes and the inner tube are retracted.

Any of the aspects herein, wherein the outer tube includes a first portion and a second portion, the first portion configured to detach from the second portion and remain in the extended position when the second portion is retracted.

Any of the aspects herein, wherein the body comprises a first end and a second end, the tool further comprises: a blade positioned at the first end and operable to cut through soft tissue, and the plurality of tubes is positioned at the second end.

Any of the aspects herein, wherein the inner tube includes a conical end.

A cannulation system according to at least one embodiment of the present disclosure comprises: a surgical tool having a body, a plurality of tubes removably secured to the body, each tube moveable from a retracted position to an extended position, the plurality of tubes including an inner tube, an outer tube, and a set of tubes positioned between the inner tube and the outer tube, each tube of the set of tubes nested in an adjacent tube, the outer tube positioned external to the set of tubes, and the inner tube positioned internal to the set of tubes, and a gripper rod having a gripper disposed on an end thereof; at least one processor; and at least one memory storing instructions for execution by the at least one processor that, when executed, cause the at least one processor to: cause the gripper to move each tube of the set of tubes, in sequence, from the retracted position to the extended position, and cause the gripper to move the set of tubes, simultaneously, from the extended position to the retracted position.

Any of the aspects herein, wherein the inner tube and each tube of the set of tubes comprises a protrusion on an outer surface thereof, each protrusion configured to engage a groove on an inner circumference of an adjacent tube.

Any of the aspects herein, further comprising a motor configured to cause the gripper rod to selectively extend and retract.

Any of the aspects herein, further comprising an oscillation rail mounted to the body that causes the gripper rod to oscillate during an extension or retraction movement.

Any of the aspects herein, wherein the gripper is reconfigurable from a first configuration to a second configuration, the gripper operable to retract the set of tubes when the gripper is in the second configuration.

Any of the aspects herein, wherein the gripper is biased towards the second configuration.

Any of the aspects herein, wherein the at least one memory stores additional instructions for execution by the at least one processor that, when executed, further cause the at least one processor to: cause the gripper to move the inner tube from the retracted position to the extended position, and cause the gripper to move the inner tube, simultaneously with the set of tubes, from the extended position to the retracted position, wherein the inner tube includes a pin on an inner surface thereof, and further wherein the gripper is configured to grip the pin when the gripper is in the second configuration to retract the inner tube and the set of tubes.

Any of the aspects herein, wherein the at least one memory stores additional instructions for execution by the at least one processor that, when executed, further cause the at least one processor to: cause the gripper to move the outer tube from the retracted position to the extended position, and wherein the outer tube is configured to remain in the extended position when the set of tubes is retracted.

A method for placing a cannula according to at least one embodiment of the present disclosure comprises: moving a first cannula from a first retracted position to a first extended position using a gripper, the first cannula comprising a knob on an outer surface thereof; moving a second cannula from a second retracted position to a second extended position using the gripper, the second cannula having a groove on an inner surface thereof that receives the knob of the first cannula when the second cannula reaches the second extended position; moving a third cannula from a third retracted position to a third extended position using the gripper; and retracting the first cannula and the second cannula, by causing the gripper to engage a pin extending from the first cannula and retracting the gripper, the engagement of the knob and the groove causing the second cannula to retract with the first cannula.

Any of the aspects herein, wherein the knob is a first knob, the groove is a first groove, the second cannula comprises a second knob on an outer surface thereof, and the method further comprises: moving a fourth cannula from a fourth retracted position to a fourth extended position using the gripper, the fourth cannula having a second groove on an inner surface thereof that receives the second knob of the second cannula when the fourth cannula reaches the fourth extended position.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 1A is an image of a cannulation device according to at least one embodiment of the present disclosure in a first position;

FIG. 1B is an image of the cannulation device of FIG. 1A in a second position;

FIG. 2A is an image of a gripper and associated structure according to at least one embodiment of the present disclosure;

FIG. 2B is an image detailing the gripper of FIG. 1B;

DETAILED DESCRIPTION

Figure 3C:
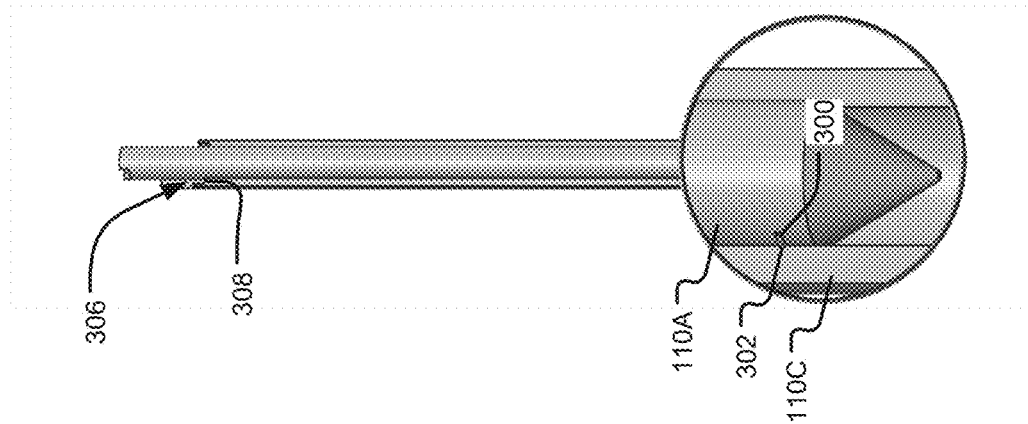
FIG. 3C is an image detailing a plurality of tubes of the cannulation device of FIG. 3B, including a detail view of a portion thereof.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

In some cases of minimally invasive surgery, endoscopy, or certain surgical procedures, it may be beneficial to create an open tube access, which may be done by placing a cannula. Placing a cannula may be done manually by cutting the skin and inserting dilators of increasing size by manually creating a linear and torque movement or by using mechanical separators. Placing the cannula requires accuracy and may take a significant amount of time. Achieving the needed accuracy frequently involves a significant radiation exposure for both a patient and a surgical team, as radiation-based imaging is used to ensure proper placement of the cannula. Further, the process of placing a cannula may be time intensive and surgeon fatigue may affect performance and operating time during later stages of the surgical operation.

Embodiments of the present disclosure provide for a motorized cannulation system that can be used to establish endoscopic access or place a tubular retractor quickly, automatically, and accurately without requiring excess radiation exposure. The system may be an electro-mechanical unit placed on a rigid base or a robotic system, using a controlled combined mechanism of skin cutting and insertion of increasing dilators using linear and oscillating movement. A robotic system can position the cannulation system in the desired position and orientation based on a planned track or trajectory. The cannulation system performs a skin cut, inserts a guiding needle, and places incrementally larger cannulae over the guide while performing gentle oscillating rotation movements during insertion. Upon achieving the required tube width, the inner cannulae are removed.

Embodiments of the present disclosure provide for a cannulation system that employs a novel mechanism to support the described functionality with, for example, a single motor and components having a small form factor such as a twisted cam follower for oscillation movement, scissor-like grippers with dual functionality for both gripping each cannula and removing the inner mechanism, and increasingly larger side knobs that allow for stages of insertion of the cannulas one tube at a time. By controlling the speed, force, and the linear advancement of the system, the process may be pre-planned to achieve the results required without manual interference. The system provides for more complete automation of percutaneous and minimally invasive procedures that will enhance procedural safety and efficiency while also simplifying training, reducing surgeon fatigue, and taking less time.

As described more fully below, methods, systems, and devices for inserting a cannula may beneficially reduce operating time by providing a streamlined automated process. The cannulation device may also improve accuracy of placing the device and may thereby reduce trauma to the surrounding patient area.

Turning first to FIG. 1, a cannulation tool or a cannulation device 100 is shown. The cannulation tool or device 100 includes a plurality of tubes 110 wherein each tube is moveable from one retracted position of a plurality of retracted positions to one extended position of a plurality of extended positions. The plurality of tubes 110 are held in the retracted position at a base 120 prior to use. In the illustrated embodiment, the plurality of tubes 110 includes an inner tube 110A, an outer tube 110B, and a set of tubes 122. In the illustrated embodiment, the set of tubes includes three tubes 110C, D, E positioned between the inner tube 110A and the outer tube 110B. In other embodiments, the set of tubes 122 includes less than three tubes or more than three tubes. The number of tubes in the set of tubes can be based on a desired size of the opening. Each tube of the set of tubes 122 is nested in an adjacent tube. The tubes 110 may be made of stainless steel, polyetheretherketone (PEEK), or any other metal, metal alloy, plastic, composite, or other material having sufficient rigidity to hold its shape during and after insertion into the body and having biocompatible properties that enable use thereof within a patient's body during a surgical procedure.

In the illustrated embodiment, the plurality of tubes 110 is disposed on a body 102 having a first end 104 and a second end 106. The body 102 may be in the form of a plate with an extension 103, as illustrated, or may be in any other form or shape including, but not limited to, a cylinder, a box, an oval, a circle, a rectangle, or the like. The first end 104 may be positioned near a skin of a patient when the body 102 is in a first position and the second end 106 may be positioned near the skin of the patient when the body 102 is in a second position. The body 102 may rotate or otherwise move between the first position and the second position. The plurality of tubes 110 may be positioned at the second end 106 and a blade 108 may be positioned at the first end 104. The blade 108 is operable to cut an incision or opening into the skin when the body 102 is in the first position.

The tool or device 100 may also include a gripper rod 118 having a gripper 200 (shown in detail in FIGS. 2A and 2B) disposed on a gripper first end 202. The gripper 200 is configured to forcibly move each tube of the plurality of tubes 110 from a respective retracted position to a respective extended position in sequence from the inner tube 110A to the outer tube 110B. The tool or device 100 may also include a motor 112 operatively connected to the gripper rod 118 and configured to cause the gripper rod 118 to selectively extend and retract. As labeled in FIG. 1B, the motor 112 is disposed on the extension 103 and spins a shaft 111 with external threads, which engages internal threads of a bracket 113. A gripper second end 204 (visible in FIG. 2A) of the gripper rod 118 is coupled to the bracket 113. The bracket 113 is also connected to a linear rail 115 adjacent and parallel to the shaft 111, which linear rail 115 assists in maintaining the bracket 113 substantially perpendicular to the shaft 111. Due to the threaded engagement of the shaft 111 with the bracket 113, rotation of the shaft 111 causes the bracket 113 to move along the shaft 111 and the linear rail 115. The second end 204 of the gripper rod 118 is rotatably connected to the bracket 113, such that movement of the bracket in a length dimension along the shaft 111 also causes movement of the gripper rod 118 along the same dimension. In some embodiments, the tool or device 100 may not include the motor 112, but may instead comprise a connector or other hookup to which an external motor may be operatively attached. The motor 112 may be an electric motor with a rotor and stator, a linear induction motor, a pneumatic motor, a hydraulic motor, a gear motor, an AC brushless motor, a DC brushed motor, a DC brushless motor, a servo motor, or the like.

The tool or device 100 may also include an oscillation rail 114 that causes the gripper rod 118 (and thus, the gripper 200) to oscillate during an extension or retraction movement (e.g., a movement in a length dimension parallel to the shaft 111). The oscillation rail 114 is positioned parallel to the shaft 111. A cam follower 116 disposed on the gripper second end 204 engages the oscillation rail 114, which forces the cam follower 116 (and thus the gripper rod 118) from side to side as the bracket 113 moves up and down the shaft 111. Such oscillation movement causes a vibration-like movement that facilitates insertion of each tube of the plurality of tubes 110 into the opening by helping to overcoming the friction and resistance of tissue surrounding the opening. Further, the oscillation rail 114 allows for the use of a smaller motor as less power is needed to insert each tube.

Turning to FIGS. 2A and 2B, the gripper rod 118 and a close up of the gripper 200 are shown. The gripper 200 includes the gripper rod 118 that extends from a gripper first end 202 to the gripper second end 204. The cam follower 116 is disposed at the gripper second end 204 and a pair of arms 208 are disposed at the gripper first end 202. Each arm of the pair of arms 208 comprises a primary arm 212 and a secondary arm 214. The primary arms 212 form a first set of gripper arms 206 when the gripper 200 is in any one of a plurality of extension positions or first configurations, including the extension position or first configuration shown in FIG. 2A, and the secondary arms 214 form a second set of gripper arms 210 when the gripper 200 is in a retracting position or a second configuration, shown in FIG. 2B. The first set of gripper arms 206 is operable to move in sequence from one of a plurality of extension positions or first configurations to another of the plurality of extension positions or first configurations (with each successive position or configuration being defined by a slightly larger distance between the tips of the primary arms 212) so as to successively move each tube of the plurality of tubes 110 from a corresponding retracted position to a corresponding extended position. The second set of gripper arms 210 is operable to move the inner tube 110A and the set of tubes 122 back to a retracted position when the gripper 200 is in the retracting position or the second configuration. As shown in the illustrated embodiment, the secondary arms 214 are shorter in length than the primary arms 212. In other embodiments, the secondary arms 214 may be longer in length that the primary arms 212 or the secondary arms 214 may be the same length as the primary arms 212.

The pair of arms 208 is biased to the retracting position or the second configuration. In some embodiments, the pair of arms 208 may be biased by a spring such as a leaf spring, coil spring, torsion spring, or the like. In the illustrated embodiment, the pair of arms 208 is biased by a torsion spring 216. In other embodiments, a portion of or all of the pair of arms 208 may be formed from a resilient material to bias the pair of arms 208 to the retracting position or the second configuration. The pair of arms 208 may be held in (or caused to move into) one of the plurality of extension positions or first configurations by a holder 304, shown in FIGS. 3A and 3B. The holder 304 may be a tab, bar, or the like. In the illustrated embodiment, the holder 304 is a plurality of pegs that prevent the gripper 200 from moving into the retracting position or the second configuration by preventing rotation of the pair of arms 208. In the illustrated embodiment, a first pair of pegs of the holder 304 are positioned closer to the plurality of tubes 110 and a second pair of pegs are positioned above the first pair of pegs (e.g., on an opposite side of the first pair of pegs from the plurality of tubes 110). The first pair of pegs are spaced further apart than the second pair of pegs such that, when the gripper rod 118 retracts sufficiently to pull the gripper 200 into the holder 304, the pair of arms 208 first contacts the first pair of pegs, which counteract the biasing force of the torsion spring 216 and push the pair of arms 208 into an extension position or the first configuration. A hump or bump in the outer contour of the pair of arms 208 (when in an extension position or the first configuration) is configured to engage the second pair of pegs, the interaction of which with the outer contour of the pair of arms 208 causes the tips of the primary arms 212 to move (against the biasing force of the torsion spring 216) even closer together. In other words, the first pair of pegs funnels the pair of arms 208 into the second pair of pegs, thereby closing the pair of arms 208. When the pair of arms 208 are uninhibited, the pair of arms 208 move to the retracting position or the second configuration.

Each tube in the plurality of tubes 110 comprises a pair of oppositely positioned slots 306 on an inner circumference thereof. The slots 306 are defined by the outer wall of the tube and by a bottom surface 308, and are wide enough (in the circumferential direction) to receive the primary arms 212 of the gripper 200. When the gripper 200 is moved downward (e.g., by operation of the motor 112, which spins the shaft 111 and causes the bracket 113 to move toward the set of tubes, thus also causing the gripper rod 118 and the gripper 200 to move in the same direction), the tips of the primary arms 212 contact the bottom surface 308 of the slot 306 of the first, inner tube 110A, and push the inner tube 110A into an extended position. The motor 112 then reverses, causing the gripper 200 to move upward within the second tube 110C (which keeps the gripper 200 in an extension position or a first configuration) until the gripper 200 reaches the slot 306 of the second tube 110C. When the gripper 200 reaches the slot 306 of the second tube 110C, the biasing force of the spring 216 pushes the tips of the primary arms 212 away from each other until they contact the outer wall of the slot 306 (which is also the outer wall of the tube 110C). The motor 112 then reverses direction again, causing the gripper 200 to push against the bottom surface 308 of the slot 306 of the second tube 110C so as to push the second tube 110C into an extended position. This process then continues until the gripper 200 has pushed all of the tubes 110 into the extended position.

Figure 3B:
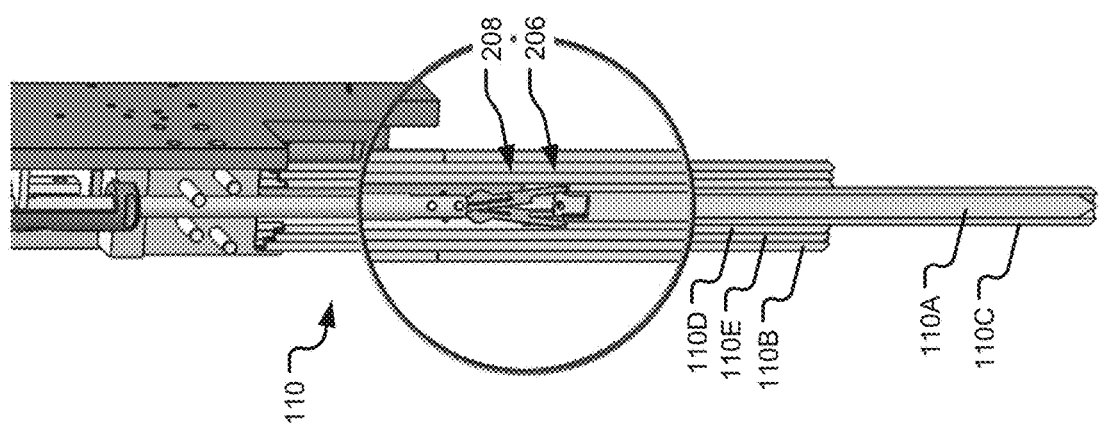
FIG. 3B is an image of a portion of a cannulation device according to at least one embodiment of the present disclosure, including a detail view of a portion thereof.
Figure 3A:
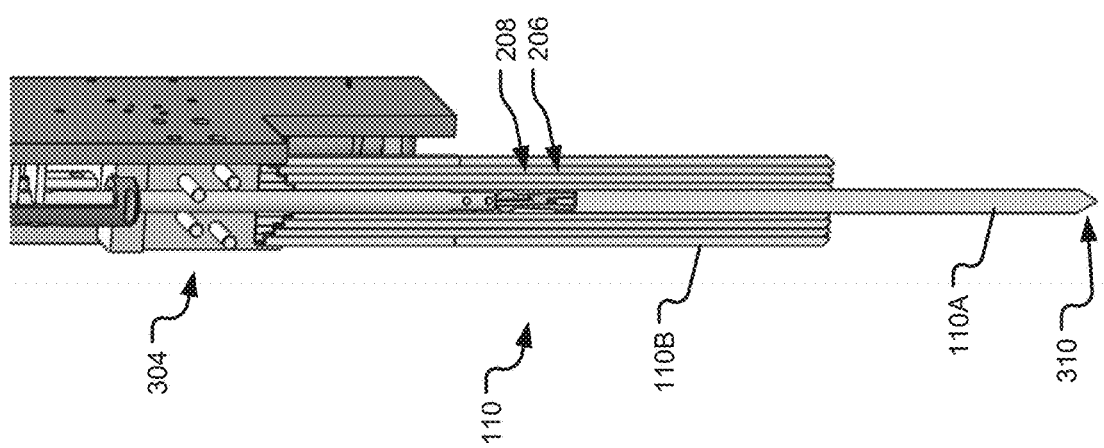
FIG. 3A is an image of a portion of a cannulation device according to at least one embodiment of the present disclosure.

Turning to FIGS. 3A-3C, the plurality of tubes 110 is shown. As previously described, the plurality of tubes 110 includes the inner tube 110A, the outer tube 110B, and the set of tubes 112 (e.g., tubes 110C, 110D, 110E) in between the inner tube 110A and the outer tube 110B. In the illustrated embodiment, the inner tube 110A includes a conical tip 310. The tip 310 may aid in insertion of the inner tube 110A into an incision or opening formed by the blade 108 (or formed in any other manner) and may act as a guide for each subsequent insertion of a tube from the plurality of tubes 110. In other embodiments, the inner tube 110A may include any shape tip such as, for example, an open conical tip, a blunt tip, a flat tip, or the like. In some embodiments, the tip of the inner tube 110A may be configured to receive a guide needle that has already been placed along the proper trajectory within the patient. In such embodiments, the inner tube 110A may be inserted over the guide needle to ensure that the inner tube 110A is inserted along the proper trajectory.

As illustrated, each tube in the plurality of tubes 110 increases in diameter from the inner tube 110A to the outer tube 110B. Each subsequent tube from the plurality of tubes 110 may also have a wedge-shaped lower or distal end to facilitate dilation of the incision or opening into which the tube is being inserted. During insertion, the incision or opening becomes wider as each tube is inserted into the incision or opening. Thus, the number of tubes in the plurality of tubes 110 may be based on the desired size of the opening (which may, in turn, be based on the size of the surgical instruments to be used during a surgical procedure that will take place, in whole or in part, through the installed cannula). In some embodiments, the plurality of tubes 110 can include two tubes and in other embodiments, the plurality of tubes can include more than two tubes 110.

The inner tube 110A and each tube of the set of tubes 122 includes a protrusion 300 positioned on an outer circumference thereof, and the outer tube 110B and each tube of the set of tubes 122 includes a groove 302 formed on an inner circumference thereof. In some embodiments, the wider the tube 110 is, the larger the corresponding protrusion 300 is. In other embodiments, each tube 110 may have the same sized protrusion 300. The protrusion 300 of one tube is removably engaged to the groove 302 of an adjacent tube. Thus, the groove 302 of each tube having such a groove 302 is sized to receive the protrusion 300 of the tube or cannula that fits immediately inside of the tube with the groove 302. Such engagement maintains each tube of the plurality of tubes 110 in the retracted position until the gripper 200 forcibly moves each tube to the extended position. The graduated size of the protrusions 300 (and corresponding grooves 302) prevents the plurality of tubes 110 from moving into the corresponding extended position as a single unit, and instead allows for one tube at a time to be moved to the corresponding extended position. This is because the force required to dislodge a smaller protrusion 300 from a smaller groove 302 is less than the force required to dislodge a larger protrusion 300 from a larger groove 302. Similarly, the protrusion 300 is also removably engaged to the groove 302 to couple a tube in the corresponding extension position to an adjacent tube when the adjacent tube is moved to the corresponding extension position. When each tube, except for the outer tube 110B, is coupled to an adjacent tube in a respective extension position, then the inner tube 110A and the set of tubes 122 can be removed as one unit from the opening, as shown in FIG. 5B.

Figure 4C:
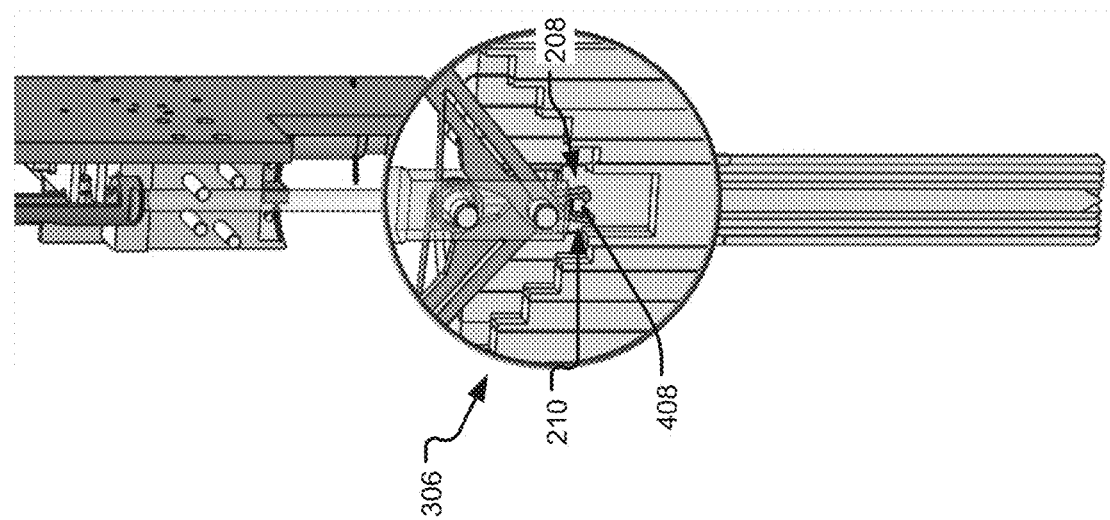
FIG. 4C is an image of a cannulation device according to at least one embodiment of the present disclosure.
Figure 4B:
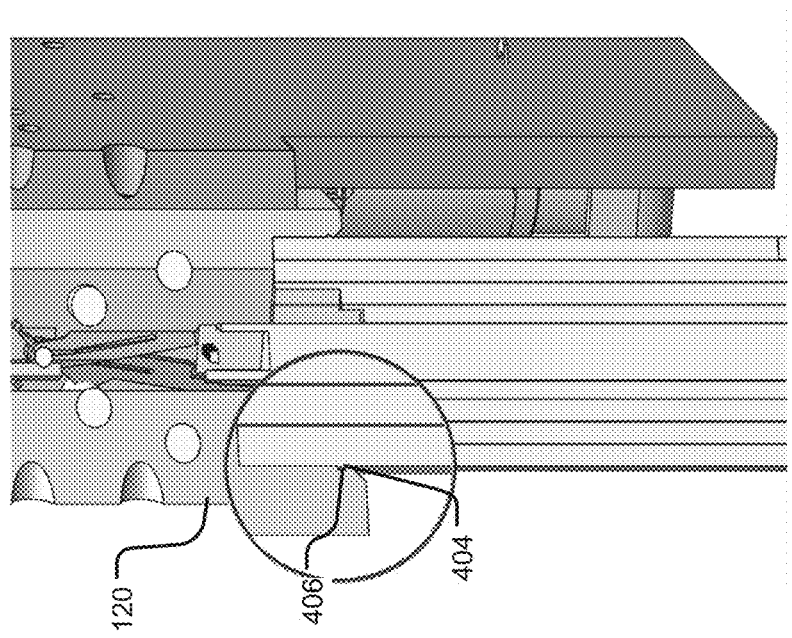
FIG. 4B is an image detailing a portion of a cannulation device according to at least one embodiment of the present disclosure.
Figure 4A:
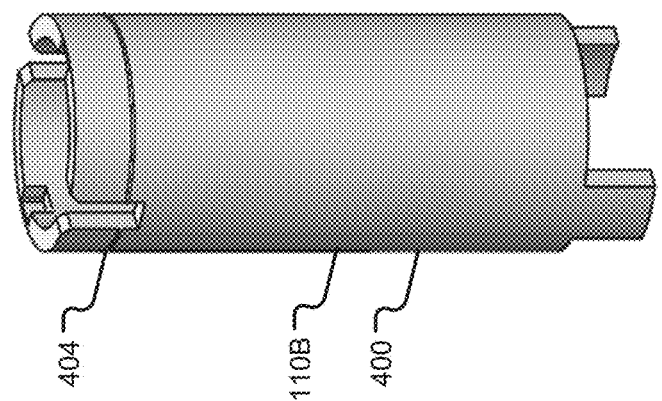
FIG. 4A is an image of one of a plurality of cannulation tubes according to at least one embodiment of the present disclosure.

Turning to FIGS. 4A and 4B, the outer tube 110B is illustrated and a detailed view of the outer tube 110B removably engaged to the base 120 are respectively shown. The outer tube 110B in some embodiments includes a first portion 400 and a second portion 402 (shown in FIG. 5A). In other embodiments, the outer tube 110B is one singular piece. In embodiments where the outer tube 110B includes the first portion 400 and the second portion 402, the first portion 400 and the second portion 402 may be removably engaged to each other. In some embodiments, such engagement results from a snap fit between the first portion 400 and the second portion 402. In other embodiments, the engagement is formed by a friction fit. In other embodiments, such engagement is enabled by a reusable adhesive (or, where the outer tube 110B is not intended for sterilization and re-use, by a non-reusable adhesive). In some embodiments a surgeon or a robot may forcibly break the first portion 400 from the second portion 402. In further embodiments, one of the first portion 400 or the second portion 402 may have a protrusion and the other one of the first portion 400 or the second portion 402 may have a groove for receiving the protrusion. In other embodiments, an outer fixation holder holds the first portion 400 and the second portion 402 and is operable to release the first portion 400.

The first portion 400 of the outer tube 110B, includes a protrusion 404 that is removably engaged to a groove 406 formed in the base 120, shown in detail in FIG. 4B. The removable engagement of the outer tube 110B to the base 120 holds the outer tube 110B in the retracted position until forced out of the retracted position by the gripper 200. Further, prior to moving any of the plurality of tubes 110 from the retracted position, the outer tube 110B holds the plurality of tubes 110 in the retracted position by way of the engagement between the outer tube 110B and the base 120 (together with the engagement of each inner tube with an adjacent tube by way of a protrusion 300 and a groove 302). The outer tube 110B may be moved from a retracted position to an extended position when the first portion 400 and the second portion 402 are engaged to each other.

FIG. 4C illustrates the pair of arms 208 in the second configuration (e.g., the second set of arms 210). When the pair of arms 208 is in the second configuration, the pair of arms 208 can grip a pin 408 protruding from an inner wall of the inner tube 110A and pull the set of tubes 122, the inner tube 110A, and the first portion 400 of the outer tube 110B from the opening, as described below. The spring 216 biases the pair of arms 208 so as to exert sufficient gripping force on the pin 408 to enable the gripper 200 to pull the inner tube 110A, the set of tubes 122, and the first portion 400 of the outer tube 110B from the opening. When the plurality of tubes 110 is removed from the opening, the first portion 400 may disengage or be caused to disengage from the second portion 402 so that the second portion 402 remains in the opening.

Figure 5A:
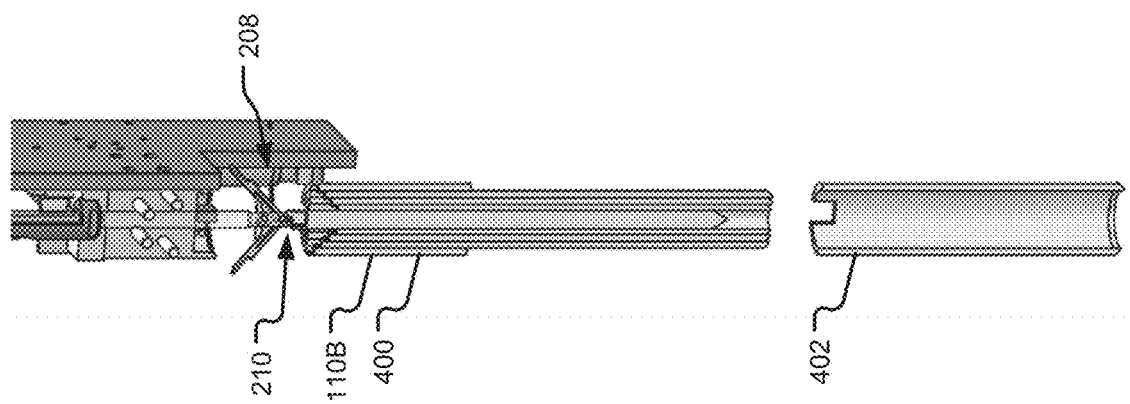
FIG. 5A is an image of a portion of a cannulation device according to at least one embodiment of the present disclosure.
Figure 5B:
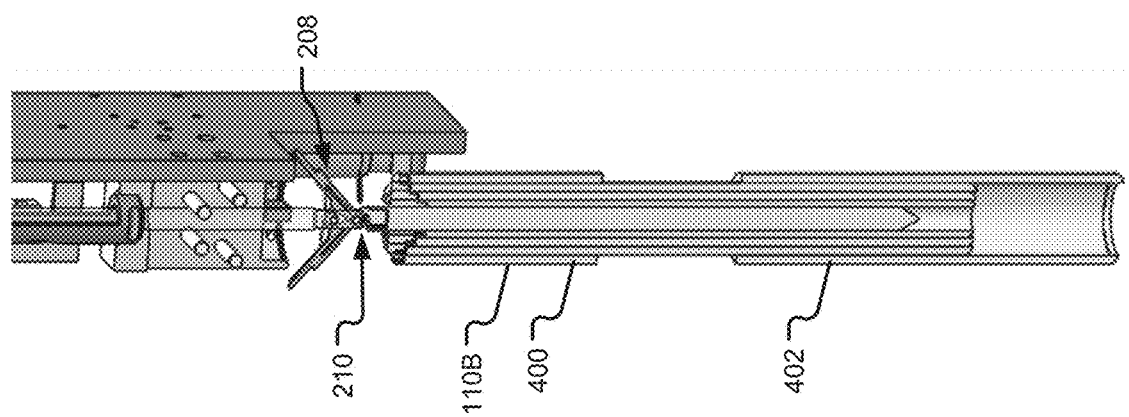
FIG. 5B is an image of a portion of a cannulation device according to at least one embodiment of the present disclosure.

Turning to FIGS. 5A and 5B, when the inner tube 110A, the set of tubes 122, and the outer tube 110B are all in the extended position, the protrusions 300 and grooves 302 of the tubes 110 are once again in engagement with each other. Once the gripper 200 has been used to place the outer tube 110B in the opening and has been retracted, the spring 216 causes the gripper 200 to reconfigure into the retracting position or second configuration. When the gripper 200 is again extended toward the tubes 110, The pair of arms 208, now in the retracting position or second configuration, grips the pin 408 of the inner tube 110A. As a result, when the tool or device 100 is pulled away from the opening, the gripper 200 pulls the set of tubes 122, the inner tube 110A, and the first portion 400 of the outer tube 110B from the opening, thereby leaving the second portion 402 of the outer tube 110B in the incision or opening. The second portion 402 of the outer tube 110B remains in the opening to keep a channel to a surgical site open and to thus provide a clean throughway for delivery or removal of fluid or samples, or insertion of a surgical tool or instrument. The second portion 402 may remain in the opening for a duration of the procedure and/or may remain in the opening after the procedure is completed.

Figure 6:
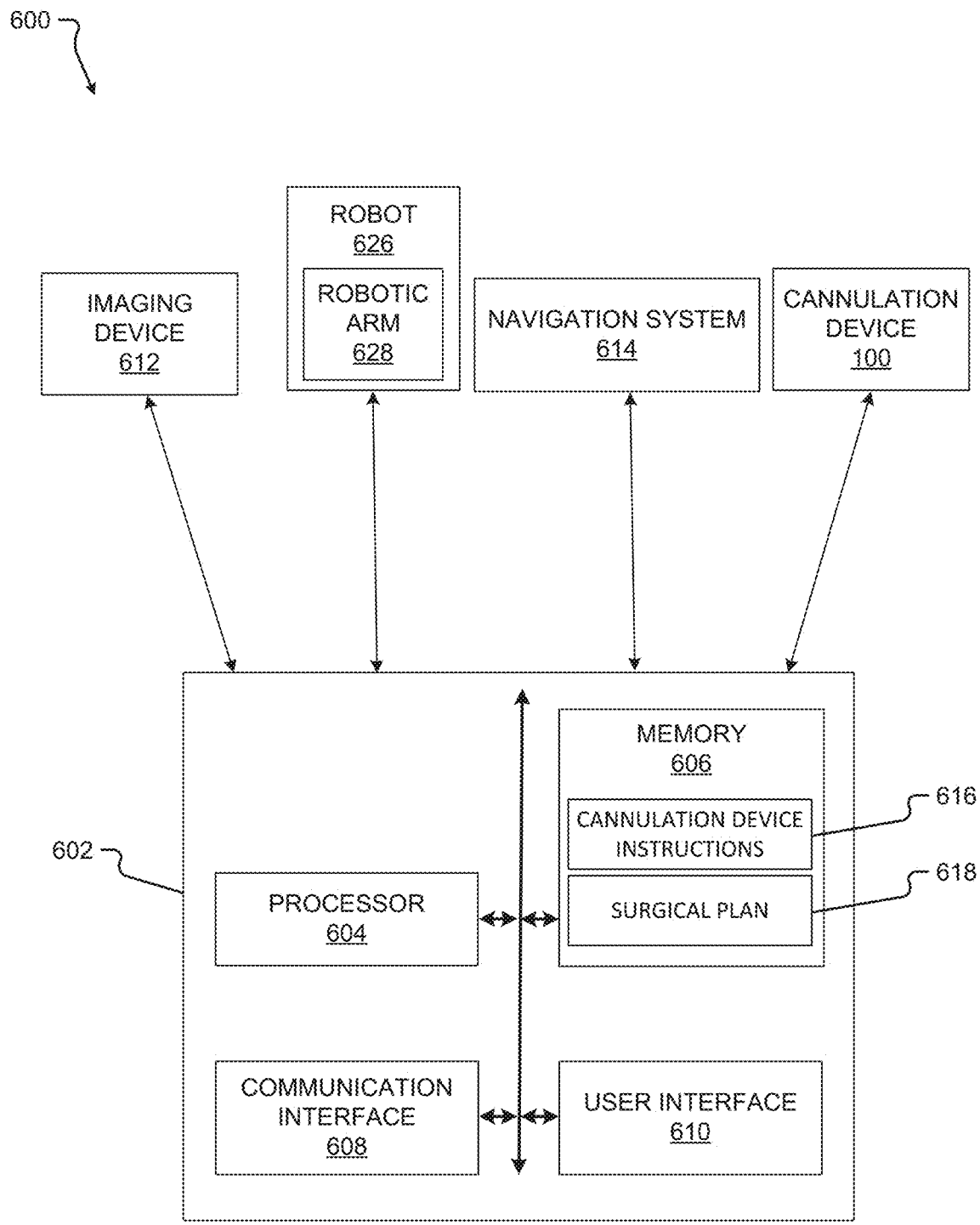
FIG. 6 is a block diagram of a system according to at least one embodiment of the present disclosure.

Turning to FIG. 6, a block diagram of a system 600 according to at least one embodiment of the present disclosure is shown. The system 600 may be used to facilitate use of the cannulation device or tool 100 with a patient. The system 600 may additionally or alternatively be used to execute cannulation device instructions 616 and/or to carry out other aspects of any method disclosed herein. The system 600 comprises a computing device 602, an imaging device 612, a navigation system 614, a robot 626, and/or a cannulation device or tool 100. The cannulation device 100 shown in FIG. 6 is the same as or substantially similar to the cannulation device 100 described above with respect to FIGS. 1A-5B. Systems according to other embodiments of the present disclosure may comprise more or fewer components than the system 600. For example, the system 600 may not include the imaging device 612, the navigation system 614, and/or the robot 626. Embodiments of the present disclosure may comprise more than one of any of the components of the system 600, including specifically the cannulation device 100, the imaging device 612, the robot 626, and/or the robotic arm 628.

The computing device 602 comprises a processor 604, a memory 606, a communication interface 608, and a user interface 610. Computing devices according to other embodiments of the present disclosure may comprise more or fewer components than the computing device 602.

The processor 604 of the computing device 602 may be any processor described herein or any similar processor. The processor 604 may be configured to execute instructions stored in the memory 606, which instructions may cause the processor 604 to carry out one or more computing steps utilizing or based on data received from the robot 626 and/or the navigation system 614.

The memory 606 may be or comprise RAM, DRAM, SDRAM, other solid-state memory, any memory described herein, or any other tangible, non-transitory memory for storing computer-readable data and/or instructions. The memory 606 may store information or data useful for completing, for example, any step of the method 700 described herein. The memory 606 may store, for example, one or more cannulation device instructions 616 and/or one or more surgical plans 618. Such instructions may, in some embodiments, be organized into one or more applications, modules, packages, layers, or engines. The instruction may cause the processor 604 to manipulate data stored in the memory 606 and/or received from the robot 626 and/or the navigation system 614.

The computing device 602 may also comprise a communication interface 608. The communication interface 608 may be used for receiving image data or other information from an external source (such as the imaging device 612, the navigation system 614, the robot 626, and in some embodiments the cannulation device or tool 100), and/or for transmitting instructions, images, or other information to an external system or device (e.g., another computing device 602, the imaging device 612, the navigation system 614, the robot 626, and/or the cannulation device or tool 100). The communication interface 608 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 608 may be useful for enabling the device 602 to communicate with one or more other processors 604 or computing devices 602, whether to reduce the time needed to accomplish a computing-intensive task or for any other reason.

The computing device 602 may also comprise one or more user interfaces 610. The user interface 610 may be or comprise a keyboard, mouse, trackball, monitor, television, touchscreen, headset, and/or any other device for receiving information from a user and/or for providing information to a user. The user interface 610 may be used, for example, to receive a user selection or other user input regarding moving an inner cannula from a retracted position to an extended position; to receive a user selection or other user input regarding moving each cannula of a set of cannulas from a respective retracted position to a respective extended position; to receive a user selection or other user input regarding moving an outer cannula from a retracted position to an extended position using the gripper; to receive a user selection or other user input regarding retracting the inner cannula and the set of cannulas; and/or to display an image, the device instructions 616, and/or the surgical plan 618. In some embodiments, the user interface 610 may be useful to allow a surgeon or other user to modify the plan 618, or other information displayed on or via the user interface 610, though it will be appreciated that each of the preceding inputs may be generated automatically by the system 600 (e.g., by the processor 604 or another component of the system 600) or received by the system 600 from a source external to the system 600. In some embodiments, user input such as that described above may be optional or not needed for operation of the systems, devices, and methods described herein.

Although the user interface 610 is shown as part of the computing device 602, in some embodiments, the computing device 602 may utilize a user interface 610 that is housed separately from one or more remaining components of the computing device 602. In some embodiments, the user interface 610 may be located proximate one or more other components of the computing device 602, while in other embodiments, the user interface 610 may be located remotely from one or more other components of the computer device 602.

The imaging device 612 may be operable to image a patient and/or the cannulation device or tool 100 to yield an image and/or image data. The imaging device 612 may be capable of taking a 2D image or a 3D image to yield the image data. "Image data" as used herein refers to the data generated or captured by an imaging device, including in a machine-readable form, a graphical form, and in any other form. In various examples, the image data may comprise data corresponding to an anatomical feature of the patient or a portion thereof and also data corresponding to the cannulation device or tool 100 for placement, insertion, and guidance of each tube of the plurality of tubes 110 during insertion. The imaging device 612 may be or comprise, for example, a fluoroscope, but may also be or comprise an ultrasound probe, an O-arm, a C-arm, a G-arm, or any other device utilizing X-ray-based imaging (e.g., a CT scanner, or other X-ray machine), a magnetic resonance imaging (MRI) scanner, an optical coherence tomography scanner, an endoscope, a telescope, a thermographic camera (e.g., an infrared camera), or any other imaging device suitable for obtaining images or image data.

The navigation system 614 may provide navigation for a surgeon and/or a surgical robot during an operation. The navigation system 614 may be any now-known or future-developed navigation system, including, for example, the Medtronic StealthStation™ S8 surgical navigation system. The navigation system 614 may include a camera or other sensor(s) for tracking one or more reference markers, navigated trackers, or other objects within the operating room or other room where a surgical procedure takes place. In various embodiments, the navigation system 614 may be used to track a position of the cannulation device or tool 100 (or, more particularly, of a navigated tracker attached, directly or indirectly, in fixed relation to the cannulation device or tool 100). The navigation system 614 may additionally or alternatively be used to track a position of the robot 626 (or, more particularly, of a navigated tracker attached, directly or indirectly, in fixed relation to the robot 626). The navigation system 614 may include a display for displaying one or more images from an external source (e.g., the computing device 602 or other source) or a video stream from a camera or other sensor of the navigation system 614. In some embodiments, the system 600 can operate without the use of navigation system 614.

The robot 626 may be any surgical robot or surgical robotic system. The robot 626 may be or comprise, for example, the Mazor X™ Stealth Edition robotic guidance system. The robot 626 may comprise a robotic arm 628. In some embodiments, the robotic arm 628 may comprise a plurality of robotic arms. For example, the robot 626 may comprise two robotic arms or more than two robotic arms. In some examples, the robotic arm 628 may hold the cannulation device or tool 100. The robot 626 (or more particularly, the robotic arm 628) may be operable to hold the cannulation device 100 in a first position and to utilize the cannulation device 100 while it is in the first position to make an incision in a patient, and then to move the cannulation device 100 to a second position and to hold the cannulation device 100 in the second position while each of the plurality of tubes is inserted into the incision. The robot 626 may enable each tube of the plurality of tubes 110 to be inserted at the same angle as the incision was made, thereby increasing accuracy of the placement of each tube and reducing trauma to the patient at the cannulation site.

Reference markers (i.e., navigation markers) may be placed on the robot 626, the robotic arm 628, the cannulation device or tool 100 or any other object in the surgical space. The reference markers may be tracked by the navigation system 614, and the results of the tracking may be used by the robot 626 and/or by an operator of the system 600 or any component thereof. In some embodiments, the navigation system 614 can be used to track other components of the system 600 (e.g., a cannulation device or tool 100, or a portion thereof) and the system 600 can operate without the use of the robot 626 (e.g., with the surgeon manually manipulating the cannulation device or tool 100).

Figure 7:
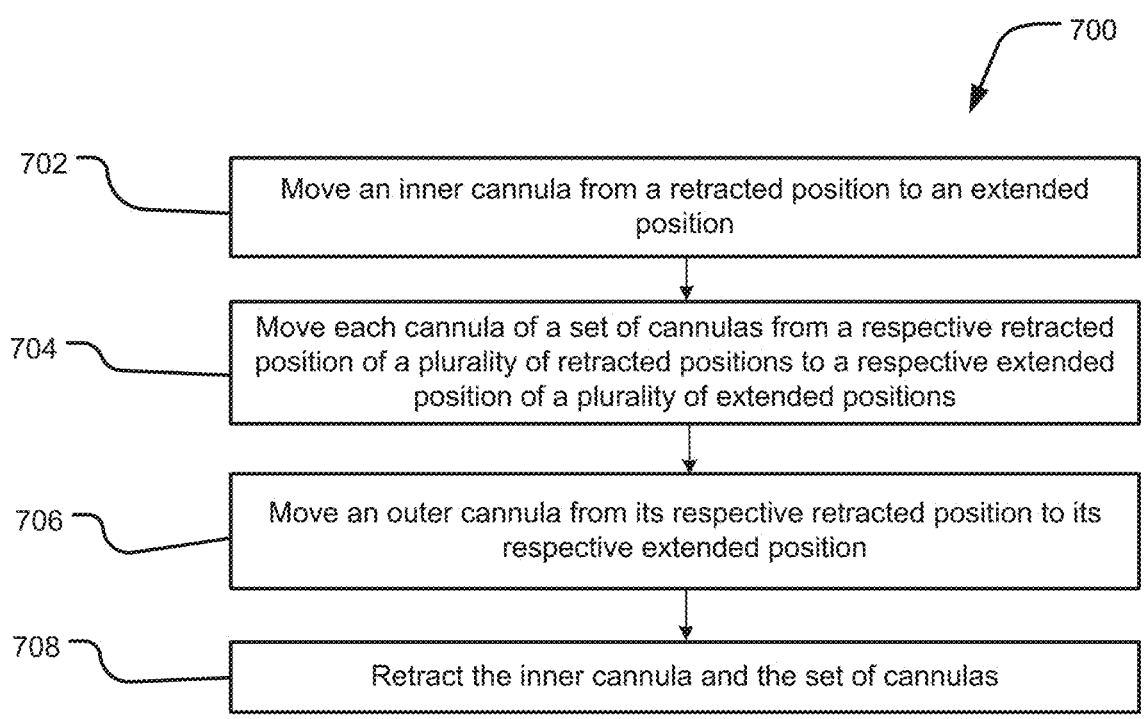
FIG. 7 is a flowchart of a method according to at least one embodiment of the present disclosure.

Turning now to FIG. 7, a method 700 for positioning a cannulation device may be executed, for example, in whole or in part, on a computing device such as the computing device 602 or a similar device, and more specifically on or by a processor such as the processor 604. Execution of the method 700 may require or utilize one or more other components of the system 600 or similar components. One or more aspects of the method 700 may be performed by or with a surgical robot such as the robot 626, a surgeon, or a combination of both.

The method 700 comprises moving an inner cannula such as the inner cannula 110A from a retracted position of a plurality of retracted positions to an extended position of a plurality of extended positions (step 702). Cannulation device instructions such as the cannulation device instructions 616 may be used by a processor such as the processor 604 to cause cannulation device 100 to move the inner cannula from the retracted position to the extended position. The inner cannula may be moved by a gripper such as the gripper 200 when the gripper is in a first configuration. The moving may include using an oscillation rail such as the oscillation rail 114 to facilitate insertion of the inner cannula into the opening by causing a rotating, back-and-forth, vibration-like motion during movement of the gripper that helps to overcome the friction and resistance of tissue surrounding the opening. The inner cannula may comprise a protrusion such as the protrusion 300 on an outer surface thereof.

The method 700 also comprises moving each cannula of a set of cannulas such as the set of a cannulas 122 from a respective retracted position of the plurality of retracted positions to a respective extended position of the plurality of extended positions (step 704). The cannulation device instructions may be used by the processor to cause each cannula of the set of cannulas to move from the retracted position to the extended position. Each cannula may be moved by the gripper when the gripper is in the first configuration (e.g., in one of a plurality of extension positions or first configurations). Each cannula may have a groove such as the groove 302 on an inner surface thereof that receives a protrusion such as the protrusion 300 of an adjacent cannula or the protrusion of the inner cannula when the adjacent cannula reaches its respective extended position of the plurality of extended positions. When the protrusion is received by the corresponding groove, the adjacent cannulas are removably engaged to each other.

The method 700 also comprises moving an outer cannula such as the outer cannula 110B from its respective retracted position of the plurality of retracted positions to its respective extended position of the plurality of extended positions (step 706). The cannulation device instructions may be used by the processor to cause the outer cannula to move from the retracted position to the extended position. The outer cannula may be moved by the gripper when the gripper is in the first configuration.

The method 700 also comprises retracting the inner cannula and the set of cannulas (step 708). The cannulation device instructions may be used by the processor to cause the inner cannula and the set of cannulas to move from the extended position to the retracted position. The inner cannula and the set of cannulas may be moved by the gripper when the gripper is in the second configuration. The outer cannula remains in the opening to keep the opening open and to provide a clear path for a surgical tool to pass through the opening. In some embodiments, the outer cannula comprises a first portion such as the first portion 400 and a second portion such as the second portion 402. In such embodiments, the retracting retracts the inner cannula, the set of cannulas, and the first portion, but leaves the second portion in the opening.

The method 700 may comprise receiving a surgical plan, which may be the same as or similar to the surgical plan 618. The surgical plan may be received via the user interface and/or the communication interface, and may be stored in the memory. The surgical plan may include information about one or more planned movements (e.g., one or more trajectories) of the cannulation device held by a robotic arm such as the robotic arm 628 during a surgical procedure. The information may also include a timeline or schedule of the one or more planned movements. The one or more planned movements may include one or more of timestamps, a type of movement (e.g., translational and/or rotational), a duration of the movement, and/or positional information (e.g., coordinates and/or orientation).

In some embodiments, the method 700 may comprise determining information about one or more needed movements (including, for example, one or more trajectories) of the cannulation device or other tool during a surgical procedure outlined or otherwise described in a surgical plan. In such embodiments, the surgical plan may not include receiving any such information via a computing device, but a processor, executing instructions stored in a memory, may generate such information based on the surgical plan.

The methods and systems described herein provide a cannulation device having a plurality of tubes that are each moveable from one of a plurality of retracted positions to one of a plurality of extended positions. By having each tube, except for an outer tube, nested and removably engaged to each other and automatically inserted, the plurality of tubes are compactly held together as one unit and the process for the insertion of each tube is streamlined. In other words, each tube does not need to be manually added to the cannulation site, which may increase overall operating time and complexity. Further, the cannulation device improves the accuracy of placement of the cannulas and reduces or eliminates additional movements caused by adding cannulation tubes to the site manually. Thus, methods, systems, and devices for placing a cannula provide for a streamlined process with improved accuracy for insertion of the cannula into a patient.

As may be appreciated based on the foregoing disclosure, the present disclosure encompasses methods with fewer than all of the steps identified in FIG. 7 (and the corresponding description of the method 700), as well as methods that include other and/or additional steps beyond those identified in FIG. 7 (and the corresponding description of the method 700). For example, the method 700 may comprise only one, or only two, of the steps 702, 704, and 706. Methods of the present disclosure explicitly include methods with one or more steps described above as part of the method 700.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A cannulation tool comprising:
   a body;
   a plurality of tubes removably secured to the body, each tube moveable from a retracted position to an extended position, the plurality of tubes including an inner tube, an outer tube, and a set of tubes positioned between the inner tube and the outer tube, each tube of the set of tubes nested in an adjacent tube, the outer tube positioned external to the set of tubes, and the inner tube positioned internal to the set of tubes;
   a gripper rod having a gripper disposed on an end thereof for forcibly moving each tube of the set of tubes, in sequence, from the retracted position to the extended position; and
   an oscillation rail mounted to the body that causes the gripper rod to oscillate during an extension or retraction movement.

2. The tool of claim 1, wherein the inner tube and each tube of the set of tubes comprises a protrusion on an outer surface thereof, each protrusion configured to engage a groove on an inner circumference of an adjacent tube.

3. The tool of claim 1, further comprising a motor configured to cause the gripper rod to selectively extend and retract.

4. The tool of claim 1, wherein the gripper moves the outer tube from the retracted position to the extended position.

5. The tool of claim 4, wherein the gripper moves the inner tube from the retracted position to the extended position.

6. The tool of claim 5, wherein the gripper is reconfigurable from a first configuration to a second configuration, the gripper operable to retract both the set of tubes and the inner tube when the gripper is in the second configuration.

7. The tool of claim 6, wherein the gripper is biased towards the second configuration.

8. The tool of claim 7, wherein the inner tube includes a pin on an inner surface thereof, and further wherein the gripper is configured to grip the pin when the gripper is in the second configuration to retract the plurality of tubes.

9. The tool of claim 6, wherein the outer tube is configured to remain in the extended position when both the set of tubes and the inner tube are retracted.

10. The tool of claim 6, wherein the outer tube includes a first portion and a second portion, the first portion configured to detach from the second portion and remain in the extended position when the second portion is retracted.

11. The tool of claim 1, wherein the body comprises a first end and a second end, the tool further comprises:
   a blade positioned at the first end and operable to cut through soft tissue, and the plurality of tubes is positioned at the second end.

12. The tool of claim 1, wherein the inner tube includes a conical end.

13. A cannulation system comprising:
   a surgical tool having a body, a plurality of tubes removably secured to the body, each tube moveable from a retracted position to an extended position, the plurality of tubes including an inner tube, an outer tube, and a set of tubes positioned between the inner tube and the outer tube, each tube of the set of tubes nested in an adjacent tube, the outer tube positioned external to the set of tubes, and the inner tube positioned internal to the set of tubes, and a gripper rod having a gripper disposed on an end thereof, and an oscillation rail mounted to the body that causes the gripper rod to oscillate during an extension or retraction movement;
   at least one processor; and
   at least one memory storing instructions for execution by the at least one processor that, when executed, cause the at least one processor to:
      cause the gripper to move each tube of the set of tubes, in sequence, from the retracted position to the extended position, and
      cause the gripper to move the set of tubes, simultaneously, from the extended position to the retracted position.

14. The system of claim 13, wherein the gripper is reconfigurable from a first configuration to a second configuration, the gripper operable to retract the set of tubes when the gripper is in the second configuration.

15. The system of claim 14, wherein the gripper is biased towards the second configuration.

16. The system of claim 14, wherein the at least one memory stores additional instructions for execution by the at least one processor that, when executed, further cause the at least one processor to:
   cause the gripper to move the inner tube from the retracted position to the extended position, and
   cause the gripper to move the inner tube, simultaneously with the set of tubes, from the extended position to the retracted position,
   wherein the inner tube includes a pin on an inner surface thereof, and further wherein the gripper is configured to grip the pin when the gripper is in the second configuration to retract the inner tube and the set of tubes.

17. The system of claim 13, wherein the at least one memory stores additional instructions for execution by the at least one processor that, when executed, further cause the at least one processor to:
   cause the gripper to move the outer tube from the retracted position to the extended position, and
   wherein the outer tube is configured to remain in the extended position when the set of tubes is retracted.

18. A system comprising:
   a robot; and
   a surgical tool for use with the robot, the surgical tool comprising;
      a body;
      a plurality of tubes removably secured to the body, each tube moveable from a retracted position to an extended position, the plurality of tubes including an inner tube, an outer tube, and a set of tubes positioned between the inner tube and the outer tube, each tube of the set of tubes nested in an adjacent tube, the outer tube positioned external to the set of tubes, and the inner tube positioned internal to the set of tubes;
      a gripper rod having a gripper disposed on an end thereof for forcibly moving each tube of the set of tubes, in sequence, from the retracted position to the extended position; and
      an oscillation rail mounted to the body that causes the gripper rod to oscillate during an extension or retraction movement.

19. The system of claim 18, wherein the gripper defines scissor-like grippers with dual functionality for both extending and retracting the plurality of tubes.

* * * * *